US012283047B2

(12) United States Patent
Campbell et al.

(10) Patent No.: US 12,283,047 B2
(45) Date of Patent: Apr. 22, 2025

(54) IMAGE MATCHING FOR FRACTURE REDUCTION

(71) Applicant: DEPUY SYNTHES PRODUCTS, INC., Raynham, MA (US)

(72) Inventors: Christopher Campbell, West Chester, PA (US); Glen Pierson, Glenmoore, PA (US); Ross Hamel, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 919 days.

(21) Appl. No.: 17/325,573

(22) Filed: May 20, 2021

(65) Prior Publication Data

US 2021/0361378 A1 Nov. 25, 2021

Related U.S. Application Data

(60) Provisional application No. 63/027,567, filed on May 20, 2020.

(51) Int. Cl.
*G06T 7/00* (2017.01)
*A61B 17/68* (2006.01)
(Continued)

(52) U.S. Cl.
CPC ............ *G06T 7/0014* (2013.01); *A61B 17/68* (2013.01); *A61B 90/36* (2016.02); *A61B 90/37* (2016.02);
(Continued)

(58) Field of Classification Search
CPC ...................... A61N 2007/0013; A61B 17/68; A61B 90/36; A61B 90/37; A61B 2017/564;
(Continued)

(56) References Cited

U.S. PATENT DOCUMENTS 6,827,721 B2 * 12/2004 Perren .................. A61B 5/1077
606/102
9,508,149 B2 11/2016 Simon et al.
(Continued)

FOREIGN PATENT DOCUMENTS

CN 106963489 7/2017
WO 2015/124171 A1 8/2015

OTHER PUBLICATIONS

Gunay et al., Cost- and time-effective three-dimensional bone-shape reconstruction from X-ray images, International Journal of Medical Robotics and Computer Assisted Surgery, 2007; 3: 323-335.
(Continued)

*Primary Examiner* — Kent Yip
(74) *Attorney, Agent, or Firm* — BakerHostetler

(57) ABSTRACT

In one example a method of fracture reduction includes imaging, intraoperatively, a fractured bone of a patient to obtain a first representation of the fractured bone in a computing system. The fractured bone defines at least a first bone fragment, and a second bone fragment that is separated from the first bone fragment by a fracture. The method includes imaging, intraoperatively, a contralateral bone of the patient to obtain a second representation of the contralateral bone in the computing system. The method includes generating, intraoperatively in the computing system, a mirrored representation of the first representation or the second representation. The first representation is compared to a representation of a desired orientation of the fractured bone, where the representation of the desired orientation is the mirrored representation of the second representation. Alternatively, the mirrored representation is compared to the representation of the desired orientation of the fractured bone, where the representation of the desired orientation is the second representation.

24 Claims, 8 Drawing Sheets

(51) Int. Cl.
*A61B 90/00* (2016.01)
*G06T 7/33* (2017.01)
*G06T 7/60* (2017.01)
*G06T 7/73* (2017.01)
*G06T 17/00* (2006.01)
*A61B 17/56* (2006.01)
*A61B 34/10* (2016.01)

(52) U.S. Cl.
CPC ............... *G06T 7/344* (2017.01); *G06T 7/60* (2013.01); *G06T 7/73* (2017.01); *G06T 17/00* (2013.01); *A61B 2017/564* (2013.01); *A61B 2017/681* (2013.01); *A61B 2034/105* (2016.02); *A61B 2090/363* (2016.02); *A61B 2090/376* (2016.02); *G06T 2207/10028* (2013.01); *G06T 2207/10116* (2013.01); *G06T 2207/20101* (2013.01); *G06T 2207/20212* (2013.01); *G06T 2207/30008* (2013.01); *G06T 2207/30204* (2013.01)

(58) Field of Classification Search
CPC ........ A61B 2017/681; A61B 2034/105; A61B 2090/363; A61B 2090/376; G06T 7/0014; G06T 7/344; G06T 7/60; G06T 7/73; G06T 2207/10028; G06T 2207/10116; G06T 2207/10081; G06T 2207/10132; G06T 2207/20101
See application file for complete search history.

(56) References Cited

U.S. PATENT DOCUMENTS

| | | |
|---|---|---|
| 9,554,868 B2 | 1/2017 | Regazzoni |
| 9,610,056 B2 | 4/2017 | Lavallee et al. |
| 9,980,783 B2 | 5/2018 | Wiets et al. |
| 10,217,217 B2 | 2/2019 | Dhruwdas |
| 10,867,436 B2 | 12/2020 | Oved |
| 2006/0241388 A1* | 10/2006 | Lavallee ............... A61B 34/20 600/416 |
| 2011/0082367 A1* | 4/2011 | Regazzoni ............ A61B 34/20 600/425 |
| 2016/0100909 A1 | 4/2016 | Wollowick et al. |
| 2016/0331463 A1 | 11/2016 | Nötzli et al. |
| 2017/0360578 A1 | 12/2017 | Shin et al. |
| 2018/0280090 A1 | 10/2018 | Davies et al. |
| 2018/0325599 A1 | 11/2018 | Seo |
| 2019/0122330 A1 | 4/2019 | Saget et al. |
| 2020/0390503 A1 | 12/2020 | Casas et al. |

OTHER PUBLICATIONS

Willis et al., 3D Reconstruction of Highly Fragmented Bone Fractures, 2007, 10 pages.
Javad Fotouhi et al: "From Perspective X-ray Imaging to Parallax-Robust Orthographic Stitching", arxiv.org, Cornell University Library, 201 Olin Library Cornell University Ithaca, NY 14853, Mar. 6, 2020 (Mar. 6, 2020), XP081615929.
Mauler Flavien et al: "Prediction of normal bone anatomy for the planning of corrective osteotomies of malunited forearm bones using a three-dimensional statistical shape model : Statistical Shape Model of the Forearm Bones", Journal of Orthopaedic Research, vol. 35, No. 12, May 4, 2017 (May 4, 2017), pp. 2630-2636, XP055820846.
Megan E. Cain et al., Prevalence of Rotational Malalignment After Inramedullary Nailing of Tibial Shaft Fractures: Can We Reliably Use the Contralateral Uninjured Side as the Reference Standard?, 102 J. of Bone and Joint Surgery 582-591 (2020).
Messmer Peter et al: "Image Fusion for Intraoperative Control of Axis in Long Bone Fracture Treatment", European Journal of Trauma, Urban & Vogel, Muenchen, DE, vol. 32, No. 6, Dec. 31, 2006 (Dec. 31, 2006), pp. 555-561, XP035803495.
Schweizer Andreas et al: "Computer-Assisted 3-Dimensional Reconstructions of Scaphoid Fractures and Nonunions With and Without the Use of Patient-Specific Guides: Early Clinical Outcomes and Postoperative Assessments of Reconstruction Accuracy", The Journal of Hand Surgery, W.B. Saunders, Amsterdam, NL, vol. 41, No. 1, Dec. 19, 2015 (Dec. 19, 2015), pp. 59-69, XP029364894.

* cited by examiner ical imaging. Preoperative and postoperative medical imaging is used for diagnosis and planning, and control, respectively. Intraoperative medical imaging, which is commonly achieved using a mobile fluoroscope, provides an optical feedback to control the manipulation of the fracture fragments, appropriate alignment and implant positioning.

IMAGE MATCHING FOR FRACTURE REDUCTION

CROSS-REFERENCE TO RELATED APPLICATIONS

This application claims the benefit of U.S. Provisional Patent Application Ser. No. 63/027,567, filed May 20, 2020, entitled "IMAGE MATCHING FOR FRACTURE REDUCTION," the entire disclosure of which is hereby incorporated by reference herein.

TECHNICAL FIELD

The present disclosure relates to systems and methods of reducing bone fractures.

BACKGROUND

Many dislocated fractures of long bones, such as of the lower extremities, are currently treated surgically (osteosynthesis) by joining bone fragments with screws, plates, nails, and/or wires. Conventional osteosyntheses typically include preoperative, intraoperative, and postoperative medical imaging. Preoperative and postoperative medical imaging is used for diagnosis and planning, and control, respectively. Intraoperative medical imaging, which is commonly achieved using a mobile fluoroscope, provides an optical feedback to control the manipulation of the fracture fragments, appropriate alignment and implant positioning.

In fractures of the lower limbs there are mainly two treatment options: closed reduction internal fixation (CRIF) and open reduction internal fixation (ORIF). In CRIF the reduction is carried out without direct exposure and direct visualization of the fracture. The only visual information about the fractured bone is provided by intraoperative fluoroscopy. In contrast, in ORIF, the fracture is exposed surgically by dissecting the overlaying soft tissues. Exposing the fracture, the surgeon can reduce it under direct vision controlling only the end result with the fluoroscope.

For many shaft fractures of tibia and femur, CRIF using intramedullary nails is the treatment of choice. In other cases, for instance where closed reduction is impossible or in institutions where no image intensifier is available, ORIF is used. Closed reduction is preferred because it is less invasive, more respectful of soft tissues, it lowers the risk of greater blood loss, interferes less with the biology of fracture healing, and shows better cosmetic results. However, CRIF is technically more demanding for the surgeon and exposes both the patient and the medical staff to higher radiation doses.

Possible complications of fixing the femoral or tibial shaft include angular and/or rotational malalignment of the fracture fragments as well as incorrect restoration of the bone length. Such complications can cause false posture, or restricted movement and/or excessive strain on the patient's joint structures due to a significant change in the natural anatomical structure and biomechanics. In many cases, the above-mentioned complications could be avoided, if improved intraoperative visualization modalities were available.

BRIEF DESCRIPTION OF THE DRAWINGS

The following description of the illustrative embodiments may be better understood when read in conjunction with the appended drawings. It is understood that potential embodiments of the disclosed systems and methods are not limited to those depicted.

DETAILED DESCRIPTION OF ILLUSTRATIVE EMBODIMENTS

Interoperative Fracture Reduction

In conventional osteosyntheses, preoperative imaging and preoperative planning can have several drawbacks. For example, preoperative imaging and planning consumes valuable time that might be needed in cases of more urgent fracture reductions. Also, the time consumed by preoperative imaging and planning could otherwise be used by the medical professional to treat other patients. As another example, preoperative imaging can result in additional radiation exposure for medical professionals and patients that could otherwise be avoided if preoperative imaging were eliminated. As yet another example, a patient's anatomy can change between preoperative imaging/planning and the actual reduction procedure. For instance, bone fragments can move relative to one another due to general settling of the bone fragments or due to movement of the patient from, for example, a preoperative setting to an operating room, or from a hospital bed to an operating table. Failure to take into account such changes can result in improper fracture reduction. Alternatively, taking into account such changes can increase the amount of time needed to reduce the fracture. Therefore, it would be desirable to eliminate preoperative imaging and planning from osteosyntheses to avoid these drawbacks.

Figure 1:
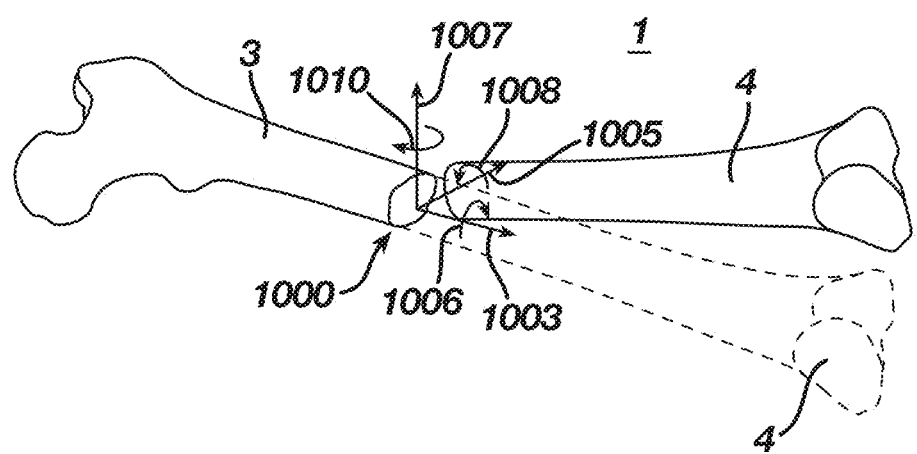
FIG. 1 depicts a schematic perspective view of a fractured bone having a proximal bone fragment and a distal bone fragment with a correct orientation of the distal bone fragment shown in phantom.

Referring initially to FIG. 1, one example of a fractured bone 1 is illustrated. In this particular example, the bone 1 is a long bone, and the fracture is located along a diaphysis (i.e., shaft) of the bone 1. The fractured bone 1 has a proximal bone fragment 3 separated from a distal bone fragment 4. The bone 1 can include, but is not necessarily limited to, bones in the leg such as the femur and tibia, or bones of the arm such as the humerus, the ulna, and the radius. It will be understood that the bone could be a bone other than a long bone, such as a rib or clavicle, and the fracture can be located on a portion of the bone other than the shaft such as on the epiphysis or metaphysis. An outline of the distal bone fragment 4' in the desired aligned position is indicated in a dotted line. An offset between the proximal bone fragment 3 and the distal bone fragment 4 can be defined by a system of coordinates 1000. The coordinates 1000 include a longitudinal axis 1003 that extends generally parallel to the fractured bone when in a nonfractured state, a lateral axis 1005 that extends substantially perpendicular to the longitudinal axis 1003, and a transverse axis 1007 that extends substantially perpendicular to the longitudinal axis 1003 and the transverse axis 1005.

Intraoperatively, the reduction of the malalignment can be performed with respect to a number of degrees of freedom. For instance, the distance between the bone fragments 3 and 4 along the longitudinal axis 1003 may be shortened or lengthened. Deviations in the angular direction 1006 about longitudinal axis 1003 may be adjusted via external or internal rotation of one or both bone fragments 3 and 4. Deviations in the angular direction 1008 about lateral axis 1005 may be adjusted via external or internal rotation of one or both bone fragments 3 and 4. Deviations in the angular direction 1010 about transverse axis 1007 may be adjusted via external or internal rotation of one or both bone fragments 3 and 4.

Figure 2:
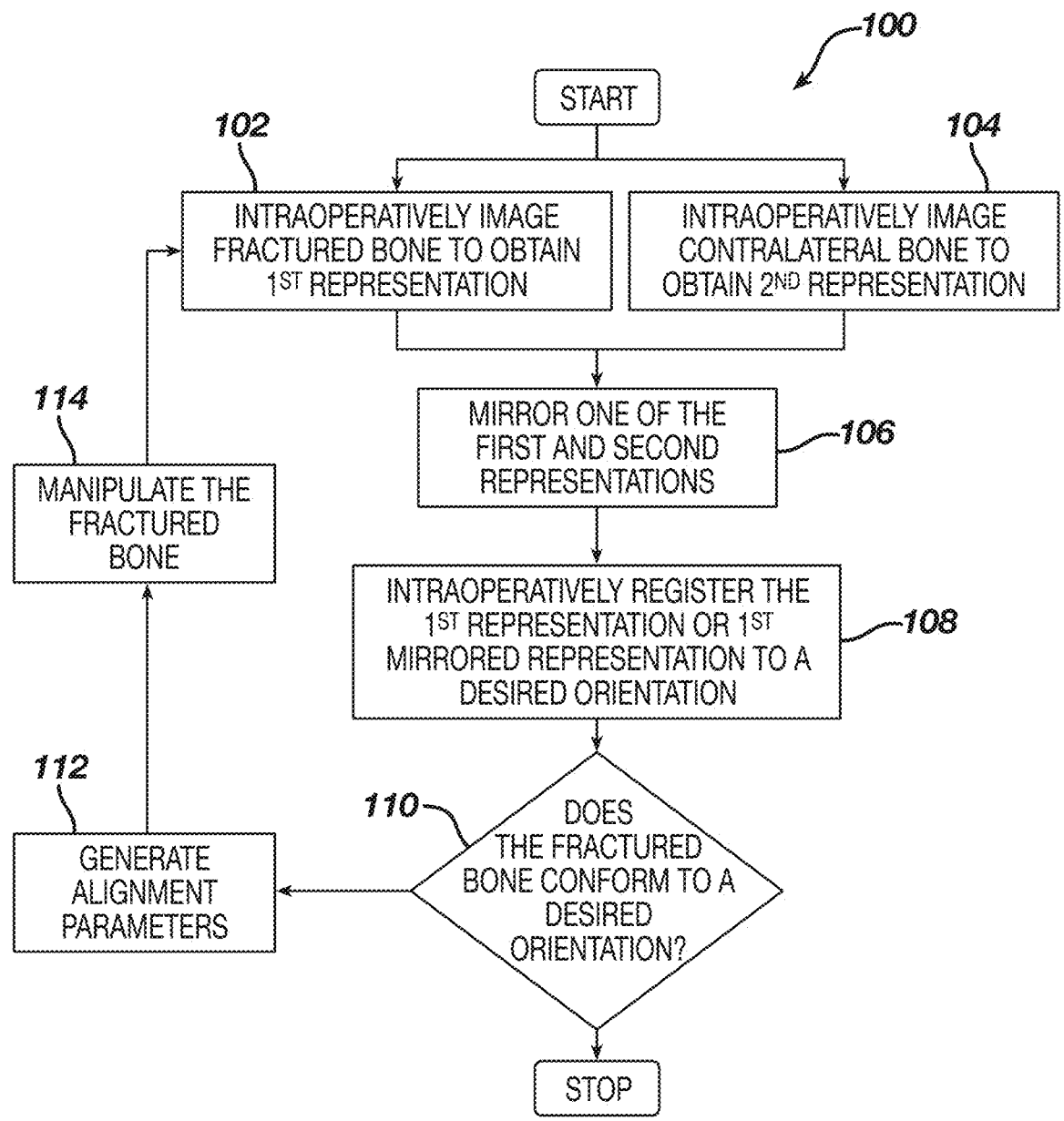
FIG. 2 shows a simplified flow diagram of a method of intraoperatively reducing a malalignment of a fractured bone of a patient is shown according to one example.

Turning now to FIG. 2, a method 100 of intraoperatively reducing a malalignment of a fractured bone of a patient is shown according to one example. The method 100 can be performed for the fracture shown in FIG. 1 or for any of the fractures discussed above in relation to FIG. 1. The method comprises a step 102 of imaging, intraoperatively, the fractured bone to obtain a first representation of the fractured bone in a computing system (an example of a computing system is discussed below in relation to FIG. 10). As used herein, the terms "intraoperative," "intraoperatively," and derivatives thereof refer to the performance of a step or procedure during the course of a surgical operation. In one example, the terms "intraoperative," "intraoperatively," and derivatives thereof can refer a step or procedure that is performed while the patient is in the operating room in which the fracture is performed. In other words, the terms "intraoperative," "intraoperatively," and derivatives thereof excludes steps or procedures that are performed before the patient is moved to the operating room in which the fracture reduction is performed.

Step 102 can comprise imaging the fractured bone one or more times to obtain one or more images. The one or more images can comprise x-ray images, CT images, ultrasound images, and/or any other suitable medical images. The one or more images can comprise a plurality of images. For example, the plurality of images can comprise at least 1) a first image taken at a first angle relative to the fractured bone and 2) a second image taken at a second angle relative to the fractured bone, different from the first angle. The first and second images can be taken at angles that are substantially perpendicular to one another, although other angles are possible. In one example, one of the first and second images can be taken along an anterior-posterior direction, and the other one of the first and second images can be taken along a lateral-medial direction. Additionally, or alternatively, each of the plurality of images can correspond to a different portion of the fractured bone, and step 102 can comprise generating the first representation by combining the plurality of images to form a representation of an entirety of the fractured bone.

Step 102 can comprise a step of generating, in the computing system, a first computer model of the fractured bone from the one or more images. The computer model can be a 2D computer model, or more preferably, a 3D computer model. Additionally, or alternatively, step 102 can comprise generating a set of digital data from the one or more images that characterizes a shape of the fractured bone. Thus, the first representation can comprise one or more, up to all, of (1) one or more images of the fractured bone, (2) a computer model of the fractured bone, and (3) a set of digital data that characterizes or defines the fractured bone.

The method 100 comprises a step 104 of imaging, intraoperatively, a contralateral bone of the patient to obtain a second representation of the contralateral bone in the computing system. As used herein, the term "contralateral" refers to the corresponding bone on the opposite of the body. For example, if the fractured bone is the patient's right femur, then the contralateral bone is the patient's left femur. Step 104 can comprise imaging the fractured bone one or more times to obtain one or more images. The one or more images can comprise x-ray images, CT images, ultrasound images, and/or any other suitable medical images. The one or more images can comprise a plurality of images. For example, the plurality of images can comprise at least 1) a first image taken at a first angle relative to the contralateral bone and 2) a second image taken at a second angle relative to the contralateral bone, different from the first angle. The first and second images can be taken at angles that are substantially perpendicular to one another, although other angles are possible. In one example, one of the first and second images can be taken along an anterior-posterior direction, and the other one of the first and second images can be taken along a lateral-medial direction. Additionally, or alternatively, each of the plurality of images can correspond to a different portion of the contralateral bone along a length of the contralateral bone, and step 104 can comprise generating the first representation by combining the plurality of images to form a representation of longer portion of the contralateral bone such as an entirety of the contralateral bone.

Step 104 can comprise a step of generating, in the computing system, a second computer model of the contralateral bone from the one or more images. The computer model can be a 2D computer model, or more preferably, a 3D computer model. Additionally, or alternatively, step 104 can comprise generating a set of digital data from the one or more images that characterizes a shape of the contralateral bone. Thus, the second representation can comprise one or more, up to all, of (1) one or more images of the contralateral bone, (2) a computer model of the contralateral bone, and (3) a set of digital data that characterizes or defines the contralateral bone.

The method 100 comprises a step 106 of generating, intraoperatively in the computing system, a mirrored representation of the first representation or the second representation. Step 106 can be performed by mirroring one of the first and second representations. Preferably, step 106 is performed by mirroring one or more, up to all, of (1) the one or more images of the contralateral bone, (2) the computer model of the contralateral bone, and (3) the set of digital data that characterizes or defines the contralateral bone. However, in alternative embodiments, step 106 can instead comprise mirroring one or more, up to all, of (1) the one or more images of the fractured bone, (2) the computer model of the fractured bone, and (3) the set of digital data that characterizes or defines the fractured bone.

The method 100 comprises a step 108 of registering, intraoperatively in the computing system, the first representation of the fractured bone to a representation of a desired orientation of the fractured bone to develop a comparison for use in reducing the fracture, wherein the representation of the desired orientation is the mirrored representation of the second representation. As used here, the terms "registering," "registration," and derivatives thereof refer to the accurate matching or superimposition of two or more images, two or more computer models, or two or more digital data sets. In an alternative example, where the first representation is mirrored in step 106, rather than the second representation, and the step 108 comprises registering, intraoperatively in the computing system, the mirrored representation of the fractured bone to a representation of a desired orientation of the fractured bone to develop a comparison for use in reducing the fracture, wherein the representation of the desired orientation is the second representation. In either example, the representation of the desired orientation that is used to reduce the fracture is generated intraoperatively, not pre-operatively.

In one example, the first representation (or mirrored representation) of the fractured bone is a computer model and the representation of the desired orientation is an image, and step 108 comprises overlaying the computer model and the image over one another. In another example, the first representation (or mirrored representation) of the fractured bone and the representation of the desired orientation are each computer models, and step 108 comprises overlaying the computer models over one another. In yet another example, the first representation (or mirrored representation) of the fractured bone and the representation of the desired orientation are each data sets, and step 108 comprises matching the data of the data sets.

In performing the registration, step 108 can comprise matching the first bone fragment 3 of the first representation (or mirrored representation) with the representation of the desired orientation. Matching can be performed using a shape matching algorithm, a best fit algorithm, or any suitable algorithm. The first representation (or mirrored representation) of the fractured bone and the representation of the desired orientation can be matched with one another by matching fiduciary markers of the first representation (or mirrored representation) with fiduciary markers of the representation of the desired orientation. The fiduciary markers of the first representation (or mirrored representation) of the fractured bone and the representation of the desired orientation can be defined by anatomical features of the fractured bone and contralateral bone. Alternatively, the fiduciary markers of the first representation (or mirrored representation) of the fractured bone and the representation of the desired orientation can be defined by artificial markers that are attached to the fractured bone and contralateral bone.

In step 110, the first representation (or mirrored representation) of the fractured bone is compared to the representation of the desired orientation. For example, the overall shape of the first representation (or mirrored representation) of the fractured bone can be compared to the representation of the desired orientation. If the first representation (or mirrored representation) of the fractured bone conforms to the representation of the desired orientation, then fracture reduction may stop.

If, on the other hand, the first representation (or mirrored representation) of the fractured bone does not conform to the representation of the desired orientation, then a set of one or more malalignment parameters are generated intraoperatively by the computing system in step 112. In one example, the malalignment parameters can define one or both of (1) a dimensional offset, such as a length, or (2) a rotational offset between the second bone fragment 4 of the first representation (or mirrored representation) of the fractured bone and the representation of the desired orientation.

The set of one or more malalignment parameters can comprise a parameter that corresponds to a difference in a length (e.g., an overall length) between the fractured bone and the contralateral bone. Additionally, or alternatively, the set of one or more malalignment parameters can comprise a parameter that corresponds to a width of the fracture measured from the first bone fragment of the fractured bone to the second bone fragment of the fractured bone. Additionally, or alternatively, the set of one or more malalignment parameters can comprise a parameter that corresponds to a difference in rotation between a portion of the fractured bone and the contralateral bone about an axis that extends along a lateral-medial direction. Additionally, or alternatively, the set of one or more malalignment parameters can comprise a parameter that corresponds to a difference in rotation between a portion of the fractured bone and the contralateral bone about an axis that extends along an anterior-posterior direction. Additionally, or alternatively, the set of one or more malalignment parameters can comprise a parameter that corresponds to a difference in rotation between a portion of the fractured bone and the contralateral bone about an axis that extends along a cranial-caudal direction.

In step 114, the set of one or more malalignment parameters can be displayed to a medical professional on, for example, a tablet, desktop or laptop computer, computer screen, or headset such as a virtual reality or augmented reality headset. The medical professional can then manipulate the fractured bone based on the one or more malalignment parameters. Alternatively, a robot can manipulate the fractured bone based on the one or more malalignment parameters. After step 114, steps 106 to 110 can be repeated to determine whether the manipulated fractured bone conforms to the desired orientation. If the manipulated fractured bone conforms to the desired orientation, then manipulation may be stopped. Otherwise, steps 112 and 114 can be performed to further manipulate the fractured bone.

Reduction of Intraarticular Fractures

Figure 3:
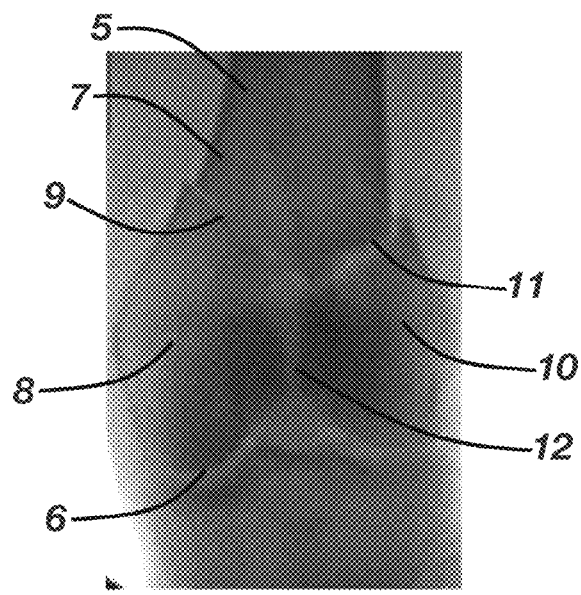
FIG. 3 shows an x-ray image of a joint having an intraarticular fracture according to one example.

Commonly, fractures are more complex than the relatively simple shaft fracture shown in FIG. 1. For example, a fracture can include multiple fracture lines, multiple bone fragments, and/or fracture lines that extend into an articular surface of a joint. FIG. 3 illustrates an exemplary fractured bone 5 that has an intraarticular fracture in which the fracture crosses into the articular surface 6 of the joint. In this example, the fracture extends along the epiphysis of the bone 5 and divides the bone 5 into a first bone fragment 7, a second bone fragment 8 that is separated from the first bone fragment 7 by a first fracture line 9. The fracture can further divide the bone 5 into a third bone fragment 10 that is separated from (1) the first bone fragment 7 by a second fracture line 11, and (2) the second bone fragment 8 by a third fracture line 12. The third fracture line 21 extends to the articular surface 6 of the bone 5. The second bone fragment 8 can comprise at least a portion of the articular surface 6. As such, when the second bone fragment 8 is separated from the first bone fragment 7, the fracture can result in malalignment and instability of the joint. Similarly, the third bone fragment 10 can comprise at least a portion of the articular surface 6. As such, when the third bone fragment 10 is separated from the first bone fragment 7, the fracture can result in malalignment and instability of the joint. It will be understood that, in alternative examples, the fractured bone 5 can have just two bone fragments, such as the first and second bone fragments 7 and 8, or can have more than the three bone fragments discussed above.

Figure 7:
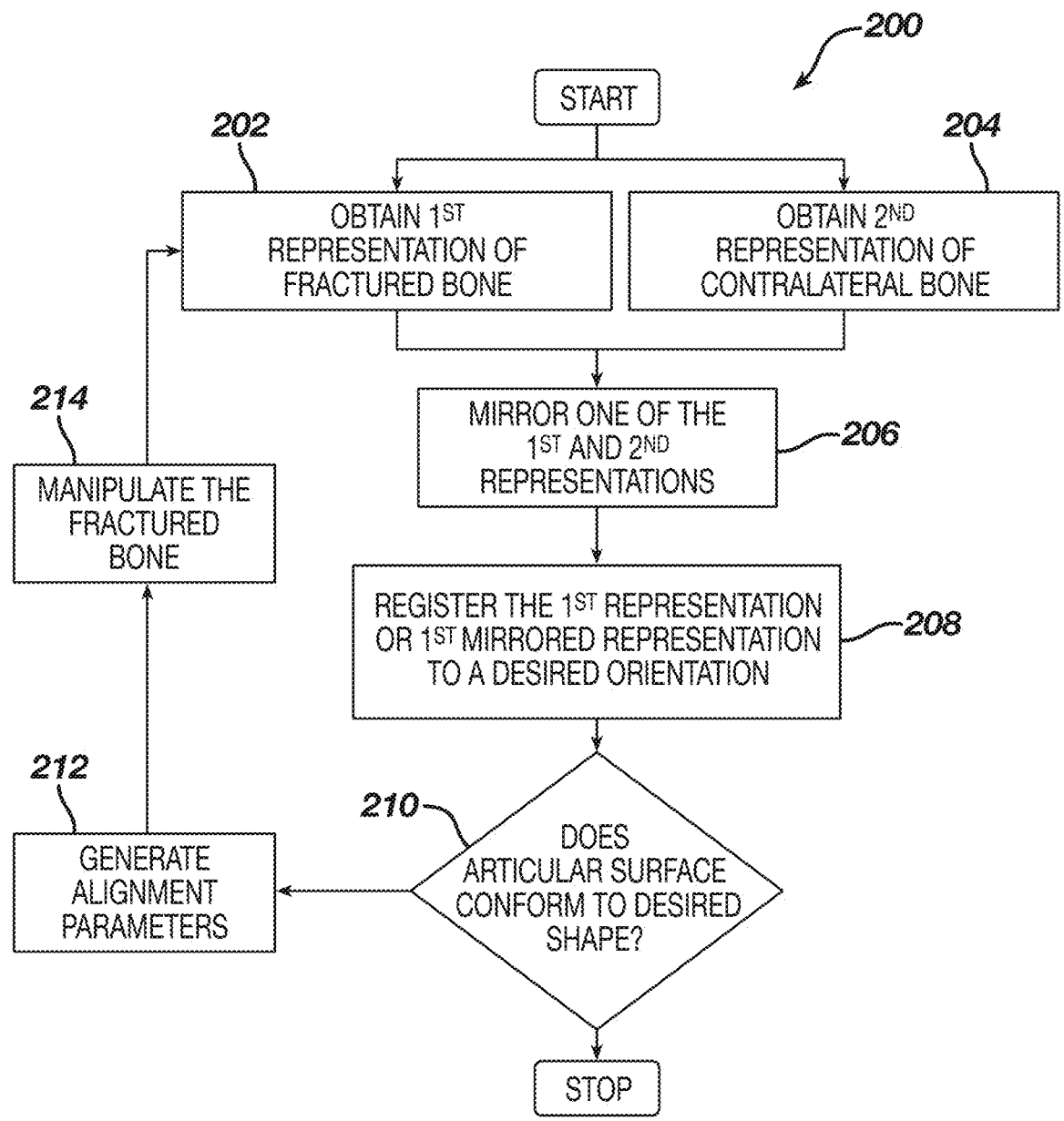
FIG. 7 shows a simplified flow diagram of a method of reducing an intraarticular fracture malalignment a patient is shown according to one example.

Turning now to FIG. 7, a method 200 of reducing an intraarticular fracture malalignment a patient is shown according to one example. The method 200 can be performed for the fracture shown in FIG. 3 or for any of other intraarticular fracture. The method 200 comprises a step 202 of obtaining a first representation of the fractured bone in a computing system (an example of a computing system is discussed below in relation to FIG. 10). Step 202 can be performed preoperatively or intraoperatively. Step 202 can comprise receiving the first representation in the computing system from another computing system, without the computing system generating the first representation.

In some examples, step 202 can comprise generating the first representation. For example, step 202 can comprise imaging the fractured bone to obtain a first representation of the fractured bone in the computing system. Step 202 can comprise imaging the fractured bone one or more times to obtain one or more images. The one or more images can comprise x-ray images, CT images, ultrasound images, and/or any other suitable medical images. The one or more images can comprise a plurality of images. For example, the plurality of images can comprise at least 1) a first image taken at a first angle relative to the fractured bone and 2) a second image taken at a second angle relative to the fractured bone, different from the first angle. The first and second images can be taken at angles that are substantially perpendicular to one another, although other angles are possible. In one example, one of the first and second images can be taken along an anterior-posterior direction, and the other one of the first and second images can be taken along a lateral-medial direction. Additionally, or alternatively, each of the plurality of images can correspond to a different portion of the fractured bone, and step 202 can comprise generating the first representation by combining the plurality of images to form a representation of an entirety of the fractured bone.

Figure 4:
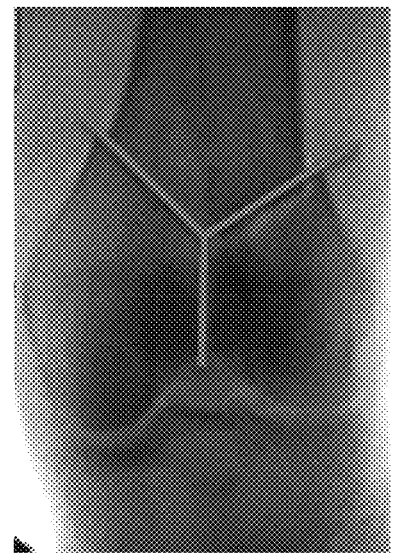
FIG. 4 shows the x-ray of FIG. 3 with the fracture lines identified.
Figure 5:
FIG. 5 shows a computer model of the joint of FIG. 3, including the intraarticular fracture of FIG. 3.
Figure 6:
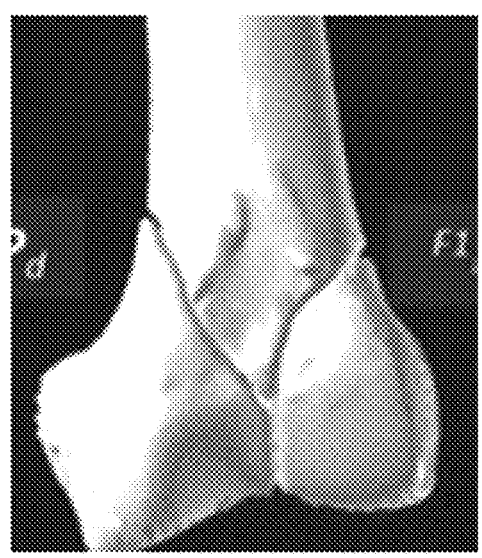
FIG. 6 shows a computer model the intraarticular fracture of FIG. 3 with the fracture reduced to a desired orientation.

Additionally, or alternatively, step 202 can comprise a step of generating, in the computing system, a first computer model of the fractured bone from the one or more images as illustrated in FIG. 5. The computer model can be a 2D computer model, or more preferably, a 3D computer model. In generating the computer model, step 202 can comprise a step of identifying the fracture lines as shown in FIG. 4. Additionally, or alternatively, step 202 can comprise generating a set of digital data from the one or more images that characterizes a shape of the fractured bone. Thus, the first representation can comprise one or more, up to all, of (1) one or more images of the fractured bone, (2) a computer model of the fractured bone, and (3) a set of digital data that characterizes or defines the fractured bone.

The method 200 comprises a step 204 of obtaining a second representation of the contralateral bone in the computing system. Step 204 can be performed preoperatively or intraoperatively. Step 204 can comprise receiving the second representation in the computing system from another computing system, without the computing system generating the second representation.

In some examples, step 204 can comprise generating the second representation. For example, step 204 can comprise imaging a contralateral bone of the patient to obtain a second representation of the contralateral bone in the computing system. Step 204 can comprise imaging the contralateral bone one or more times to obtain one or more images. The one or more images can comprise x-ray images, CT images, ultrasound images, and/or any other suitable medical images. The one or more images can comprise a plurality of images. For example, the plurality of images can comprise at least 1) a first image taken at a first angle relative to the contralateral bone and 2) a second image taken at a second angle relative to the contralateral bone, different from the first angle. The first and second images can be taken at angles that are substantially perpendicular to one another, although other angles are possible. In one example, one of the first and second images can be taken along an anterior-posterior direction, and the other one of the first and second images can be taken along a lateral-medial direction. Additionally, or alternatively, each of the plurality of images can correspond to a different portion of the contralateral bone along a length of the contralateral bone, and step 204 can comprise generating the first representation by combining the plurality of images to form a representation of longer portion of the contralateral bone such as an entirety of the contralateral bone.

Additionally, or alternatively, step 204 can comprise a step of generating, in the computing system, a second computer model of the contralateral bone from the one or more images. The computer model can be a 2D computer model, or more preferably, a 3D computer model. Additionally, or alternatively, step 204 can comprise generating a set of digital data from the one or more images that characterizes a shape of the contralateral bone. Thus, the second representation can comprise one or more, up to all, of (1) one or more images of the contralateral bone, (2) a computer model of the contralateral bone, and (3) a set of digital data that characterizes or defines the contralateral bone.

The method 200 comprises a step 206 of generating, intraoperatively in the computing system, a mirrored representation of the first representation or the second representation. Step 206 can be performed by mirroring one of the first and second representations. Preferably, step 206 is performed by mirroring one or more, up to all, of (1) the one or more images of the contralateral bone, (2) the computer model of the contralateral bone, and (3) the set of digital data that characterizes or defines the contralateral bone. However, in alternative embodiments, step 206 can instead comprise mirroring one or more, up to all, of (1) the one or more images of the fractured bone, (2) the computer model of the fractured bone, and (3) the set of digital data that characterizes or defines the fractured bone.

The method 200 comprises a step 208 of registering, in the computing system, the first representation of the fractured bone to a representation of a desired orientation of the fractured bone to develop a comparison for use in reducing the fracture, wherein the representation of the desired orientation is the mirrored representation of the second representation. In an alternative example, where the first representation is mirrored in step 206, rather than the second representation, and the step 208 comprises registering, in the computing system, the mirrored representation of the fractured bone to a representation of a desired orientation of the fractured bone to develop a comparison for use in reducing the fracture, wherein the representation of the desired orientation is the second representation.

In one example, the first representation (or mirrored representation) of the fractured bone is a computer model and the representation of the desired orientation is an image, and step 208 comprises overlaying the computer model and the image over one another. In another example, the first representation (or mirrored representation) of the fractured bone and the representation of the desired orientation are each computer models, and step 208 comprises overlaying the computer models over one another. In yet another example, the first representation (or mirrored representation) of the fractured bone and the representation of the desired orientation are each data sets, and step 208 comprises matching the data of the data sets.

In performing the registration, step 208 can comprise matching the first bone fragment 7 (see FIG. 3) of the first representation (or mirrored representation) with the representation of the desired orientation. Matching can be performed using a shape matching algorithm, a best fit algorithm, or any suitable algorithm. The first representation (or mirrored representation) of the fractured bone and the representation of the desired orientation can be matched with one another by matching fiduciary markers of the first representation (or mirrored representation) with fiduciary markers of the representation of the desired orientation. The fiduciary markers of the first representation (or mirrored representation) of the fractured bone and the representation of the desired orientation can be defined by anatomical features of the fractured bone and contralateral bone. Alternatively, the fiduciary markers of the first representation (or mirrored representation) of the fractured bone and the representation of the desired orientation can be defined by artificial markers that are attached to the fractured bone and contralateral bone.

In step 210, the first representation (or mirrored representation) of the fractured bone is compared to the representation of the desired orientation to determine whether the osteojoint line is properly aligned. For example, the articular surface of the first representation (or mirrored representation) can be compared to the articular surface of the desired orientation. Additionally, or alternatively, the overall shape of the first representation (or mirrored representation) of the fractured bone can be compared to the representation of the desired orientation. If the first representation (or mirrored representation) of the fractured bone conforms to the representation of the desired orientation, then fracture reduction may stop.

If, on the other hand, the first representation (or mirrored representation) of the fractured bone does not sufficiently conform to the representation of the desired orientation, then a set of one or more malalignment parameters are generated intraoperatively by the computing system in step 212. In one example, the malalignment parameters can define one or both of (1) a dimensional offset, such as a length, or (2) a rotational offset between the second bone fragment 8 (see FIG. 3) of the first representation (or mirrored representation) of the fractured bone and the representation of the desired orientation.

The set of one or more malalignment parameters can comprise a parameter that corresponds to a difference in length between the fractured bone and the contralateral bone. Additionally, or alternatively, the set of one or more malalignment parameters can comprise a parameter that corresponds to a width of the fracture measured from the first bone fragment of the fractured bone to the second bone fragment of the fractured bone. Additionally, or alternatively, the set of one or more malalignment parameters can comprise a parameter that corresponds to a difference in rotation between a portion of the fractured bone and the contralateral bone about an axis that extends along a lateral-medial direction. Additionally, or alternatively, the set of one or more malalignment parameters can comprise a parameter that corresponds to a difference in rotation between a portion of the fractured bone and the contralateral bone about an axis that extends along an anterior-posterior direction. Additionally, or alternatively, the set of one or more malalignment parameters can comprise a parameter that corresponds to a difference in rotation between a portion of the fractured bone and the contralateral bone about an axis that extends along a cranial-caudal direction.

In step 214, the set of one or more malalignment parameters can be displayed to a medical professional on, for example, a tablet, desktop or laptop computer, computer screen, or headset such as a virtual reality or augmented reality headset. The medical professional can then manipulate the fractured bone based on the one or more malalignment parameters. Alternatively, a robot can manipulate the fractured bone based on the one or more malalignment parameters. After step 214, steps 206 to 210 can be repeated to determine whether the manipulated fractured bone conforms to the desired orientation. If the manipulated fractured bone conforms to the desired orientation, then manipulation may be stopped. Otherwise, steps 212 and 214 can be performed to further manipulate the fractured bone.

Fracture Reduction to Correct Mechanics of the Limb

In conventional osteosyntheses, reduction of the fracture is commonly performed by focusing only on the fractured bone to ensure that the fractured bone conforms to a desired shape. However, reducing a fractured bone to a desired shape might not necessarily result in proper mechanics of the limb. In some cases, it may be desirable to reduce a fractured bone in a manner that does not conform perfectly to a desired shape so as to ensure proper mechanics of the limb. Therefore, it would be beneficial to perform an osteosynthesis by considering proper mechanics of the limb in addition, or alternatively, to considering the desired shape of the fractured bone.

Figure 8:
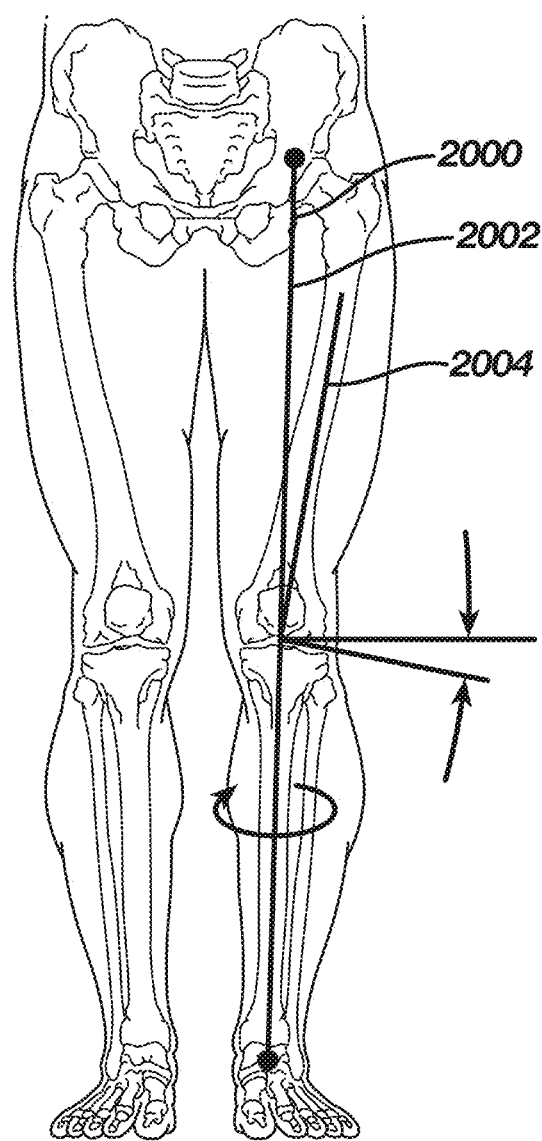
FIG. 8 shows a schematic diagram of the limbs of a lower torso, illustrating various axes of the limbs.
Figure 9:
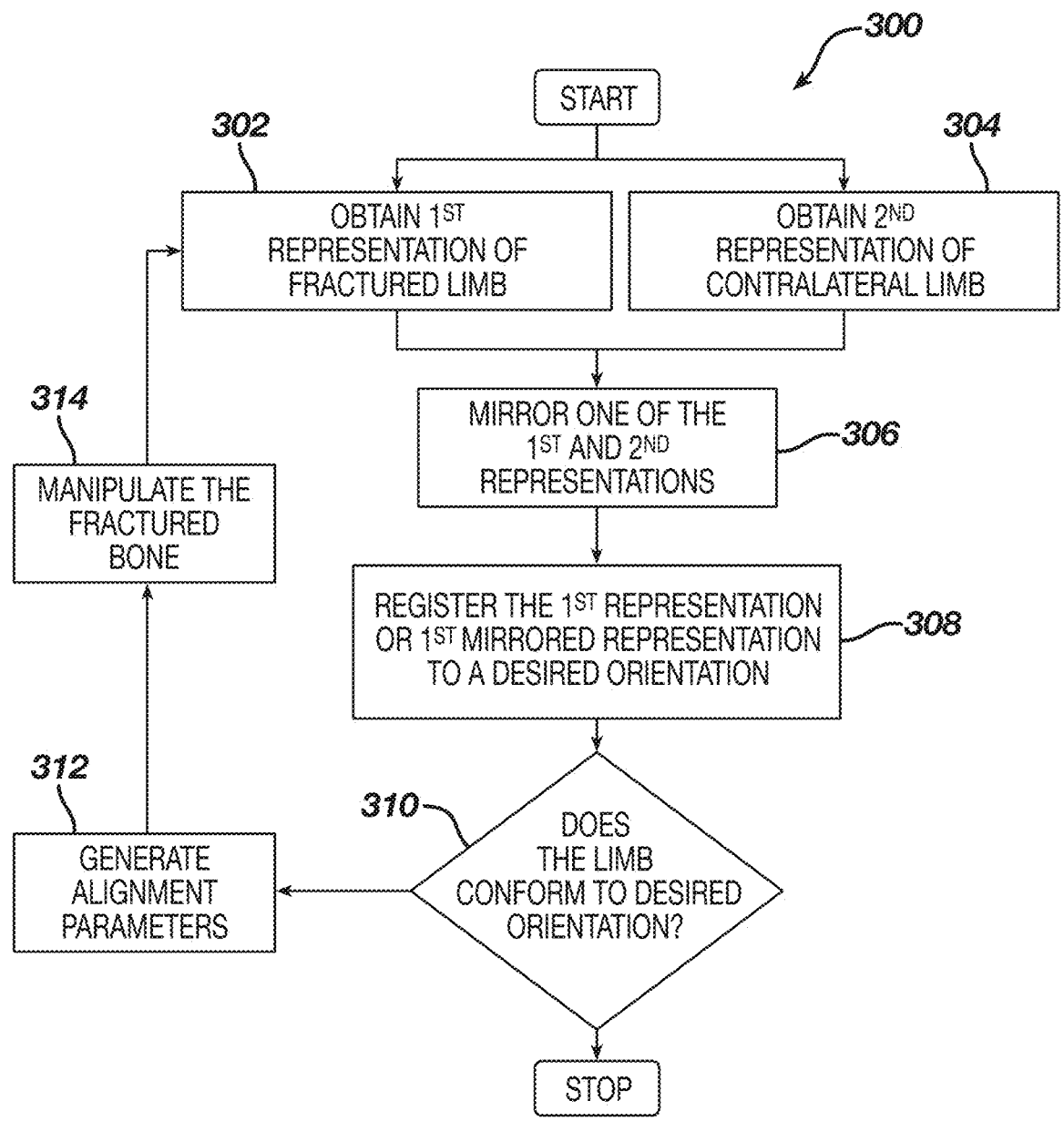
FIG. 9 shows a simplified flow diagram of a method of reducing a malalignment of a fractured bone of a limb of a patient to attain a desired mechanics of the limb according to one example.

Referring to FIGS. 8 and 9, the mechanics of a limb 20 are illustrated according to one example. In this example, the mechanics are shown relative to a leg. However, it will be understood that the mechanics can apply to other limbs, such as to an arm. The limb 20 can be defined by at least one axis, such as a plurality of axes. The at least one axis can comprise a mechanical axis of the limb that extends from a center of a head of the limb, such as the femoral or humeral head, to a center of the opposing joint, such as the ankle or wrist joint. Each long bone of the limb 20 can have a mechanical axis that generally extends from a center of one end of the bone to a center of the other end of the bone. For example, the femur can have a mechanical axis 2002 that extends from a center of the femoral head to the intercondylar notch of the distal end of the femur. Each long bone of the limb 20 can have an anatomic axis that generally extends along the intramedullary canal, bisecting the bone in half.

The at least one axis can be used to determine proper alignment of the mechanics of a limb 20 during fracture reduction. For example, the fractured bone or limb can be manipulated until the fragments of the bone align along a particular mechanical or anatomic axis of the fractured bone. As another example, an axis of the fractured bone or limb can be compared to a corresponding axis of the contralateral bone or limb to determine whether the axis of the fractured bone or limb extends along a proper angle. As yet another example, rotation of the fractured bone or limb about one or more of the axes can be compared to rotation of the contralateral bone or limb about the corresponding one or more axes. Restoration of proper joint lines through fracture reduction can ensure that the bones of a limb extend along a proper axis or proper axes.

Turning now to FIG. 9, a method 300 is shown according to one example for reducing a malalignment of a fractured bone of a limb of a patient to attain a desired mechanics of the limb. The limb can be, for example, an arm, a leg, or any other suitable limb. The method 300 can be performed for the fracture shown in FIG. 1, FIG. 3, or for any of other suitable fracture. The method 300 can be performed in conjunction with, such as before, during, or after, the method 100 of FIG. 2 and/or the method 200 of FIG. 7. In one example, the method 300 can be performed after reduction is completed in method 100 and/or the method 200. In another example, the method 300 can be performed each iteration of the method 100 and/or the method 200.

The method 300 comprises a step 302 of obtaining, in a computing system (an example of a computing system is discussed below in relation to FIG. 10), a first representation of a patient's limb having a fractured bone and an adjacent bone. The first representation includes 1) a representation of at least a portion of the fractured bone that includes the fracture and 2) a representation of at least a portion of the adjacent bone. The first representation can include a joint that adjoins the fractured bone and the adjacent bone. In some examples, the first representation can include an entirety of the fractured bone. In some examples, the first representation can include an entirety of the adjacent bone. In some examples, the first representation can include at least two joints of the limb, or at least three joints of the limb.

Step 302 can be performed preoperatively or intraoperatively. Step 302 can comprise receiving the first representation in the computing system from another computing system, without the computing system generating the first representation. Alternatively, in some examples, step 302 can comprise generating the first representation. For example, step 302 can comprise imaging the limb to obtain a first representation of the limb having the fractured bone in the computing system. Step 302 can comprise imaging the limb one or more times to obtain one or more images. The one or more images can comprise x-ray images, CT images, ultrasound images, and/or any other suitable medical images. The one or more images can comprise a plurality of images. For example, the plurality of images can comprise at least 1) a first image taken at a first angle relative to the limb and 2) a second image taken at a second angle relative to the limb, different from the first angle. The first and second images can be taken at angles that are substantially perpendicular to one another, although other angles are possible. In one example, one of the first and second images can be taken along an anterior-posterior direction, and the other one of the first and second images can be taken along a lateral-medial direction. Additionally, or alternatively, each of the plurality of images can correspond to a different portion of the limb, and step 302 can comprise generating the first representation by combining the plurality of images to form the representation of the limb.

Additionally, or alternatively, step 302 can comprise a step of generating, in the computing system, a first computer model of the limb from the one or more images. The computer model can be a 2D computer model, or more preferably, a 3D computer model. Additionally, or alternatively, step 302 can comprise generating a set of digital data from the one or more images that characterizes a shape of the limb. Thus, the first representation can comprise one or more, up to all, of (1) one or more images of the limb, (2) a computer model of the limb, and (3) a set of digital data that characterizes or defines the limb.

The method 300 comprises a step 304 of obtaining a second representation of the contralateral limb in the computing system. Step 304 can be performed preoperatively or intraoperatively. Step 304 can comprise receiving the second representation in the computing system from another computing system, without the computing system generating the second representation.

In some examples, step 304 can comprise generating the second representation. For example, step 304 can comprise imaging a contralateral limb of the patient to obtain a second representation of the contralateral limb in the computing system. Step 304 can comprise imaging the contralateral limb one or more times to obtain one or more images. The one or more images can comprise x-ray images, CT images, ultrasound images, and/or any other suitable medical images. The one or more images can comprise a plurality of images. For example, the plurality of images can comprise at least 1) a first image taken at a first angle relative to the contralateral limb and 2) a second image taken at a second angle relative to the contralateral limb, different from the first angle. The first and second images can be taken at angles that are substantially perpendicular to one another, although other angles are possible. In one example, one of the first and second images can be taken along an anterior-posterior direction, and the other one of the first and second images can be taken along a lateral-medial direction. Additionally, or alternatively, each of the plurality of images can correspond to a different portion of the contralateral limb along a length of the contralateral limb, and step 304 can comprise generating the first representation by combining the plurality of images to form the representation of the contralateral limb.

Additionally, or alternatively, step 304 can comprise a step of generating, in the computing system, a second computer model of the contralateral limb from the one or more images. The computer model can be a 2D computer model, or more preferably, a 3D computer model. Additionally, or alternatively, step 304 can comprise generating a set of digital data from the one or more images that characterizes a shape of the contralateral limb. Thus, the second representation can comprise one or more, up to all, of (1) one or more images of the contralateral limb, (2) a computer model of the contralateral limb, and (3) a set of digital data that characterizes or defines the contralateral limb.

The method 300 comprises a step 306 of generating, intraoperatively in the computing system, a mirrored representation of the first representation or the second representation. Step 306 can be performed by mirroring one of the first and second representations. Preferably, step 306 is performed by mirroring one or more, up to all, of (1) the one or more images of the contralateral limb, (2) the computer model of the contralateral limb, and (3) the set of digital data that characterizes or defines the contralateral limb. However, in alternative embodiments, step 306 can instead comprise mirroring one or more, up to all, of (1) the one or more images of the fractured limb, (2) the computer model of the fractured limb, and (3) the set of digital data that characterizes or defines the fractured limb.

The method 300 comprises a step 308 of registering, in the computing system, the first representation of the fractured limb to a representation of a desired orientation of the fractured limb to develop a comparison for use in reducing the fracture, wherein the representation of the desired orientation is the mirrored representation of the second representation. In an alternative example, where the first representation is mirrored in step 306, rather than the second representation, and the step 308 comprises registering, in the computing system, the mirrored representation of the fractured limb to a representation of a desired orientation of the fractured limb to develop a comparison for use in reducing the fracture, wherein the representation of the desired orientation is the second representation.

In one example, the first representation (or mirrored representation) of the fractured limb is a computer model and the representation of the desired orientation is an image, and step 308 comprises overlaying the computer model and the image over one another. In another example, the first representation (or mirrored representation) of the fractured limb and the representation of the desired orientation are each computer models, and step 308 comprises overlaying the computer models over one another. In yet another example, the first representation (or mirrored representation) of the fractured limb and the representation of the desired orientation are each data sets, and step 308 comprises matching the data of the data sets.

In performing the registration, step 308 can comprise matching at least a portion of the first representation (or mirrored representation) with the representation of the desired orientation. Matching can be performed using a shape matching algorithm, a best fit algorithm, or any suitable algorithm. The first representation (or mirrored representation) of the fractured limb and the representation of the desired orientation can be matched with one another by matching fiduciary markers of the first representation (or mirrored representation) with fiduciary markers of the representation of the desired orientation. The fiduciary markers of the first representation (or mirrored representation) of the fractured limb and the representation of the desired orientation can be defined by anatomical features of the fractured limb and contralateral limb. Alternatively, the fiduciary markers of the first representation (or mirrored representation) of the fractured limb and the representation of the desired orientation can be defined by artificial markers that are attached to the fractured limb and contralateral limb.

In step 310, the first representation (or mirrored representation) of the fractured limb is compared to the representation of the desired orientation to determine whether the overall mechanics of the fractured limb are within a desired limit or range. For example, an overall length of the first representation (or mirrored representation) can be compared to an overall length of the desired orientation. Additionally, or alternatively, one or more axes of the limb in the first representation (or mirrored representation) can be compared to one or more corresponding axes of the representation of the desired orientation to determine whether the axes are aligned within a desired limit or range. Additionally, or alternatively, the first representation (or mirrored representation) can be compared to the representation of the desired orientation to determine whether rotation of the limb of the first representation (or mirrored representation) about one or more axes is within a desired limit or range of a corresponding rotation of the representation of the desired orientation.

If the first representation (or mirrored representation) of the fractured bone conforms to the representation of the desired orientation, then fracture reduction may stop. If, on the other hand, the first representation (or mirrored representation) of the fractured bone does not sufficiently conform to the representation of the desired orientation, then a set of one or more malalignment parameters are generated intraoperatively by the computing system in step 312. In one example, the malalignment parameters can define one or both of (1) a dimensional offset, such as a length, or (2) a rotational offset between the first representation (or mirrored representation) of the fractured limb and the representation of the desired orientation.

The set of one or more malalignment parameters can comprise a parameter that corresponds to a difference in length between the fractured limb and the contralateral limb. Additionally, or alternatively, the set of one or more malalignment parameters can comprise a parameter that corresponds to a deviation between an axis of the fractured limb and a corresponding axis of the contralateral limb. Additionally, or alternatively, the set of one or more malalignment parameters can comprise a parameter that corresponds to a difference in rotation between the fractured limb and the contralateral limb about an axis that extends along a lateral-medial direction. Additionally, or alternatively, the set of one or more malalignment parameters can comprise a parameter that corresponds to a difference in rotation between the fractured limb and the contralateral limb about an axis that extends along an anterior-posterior direction. Additionally, or alternatively, the set of one or more malalignment parameters can comprise a parameter that corresponds to a difference in rotation between a portion of the fractured limb and the contralateral limb about an axis that extends along a cranial-caudal direction.

In step 314, the set of one or more malalignment parameters can be displayed to a medical professional on, for example, a tablet, desktop or laptop computer, computer screen, or headset such as a virtual reality or augmented reality headset. The medical professional can then manipulate the fractured limb based on the one or more malalignment parameters. Alternatively, a robot can manipulate the fractured limb based on the one or more malalignment parameters. After step 314, steps 306 to 310 can be repeated to determine whether the mechanics of the manipulated fractured limb are within a desired limit or range. If the manipulated fractured limb conforms to the desired orientation, then manipulation may be stopped. Otherwise, steps 312 and 314 can be performed to further manipulate the fractured bone.

Fracture Reduction System

Figure 10:
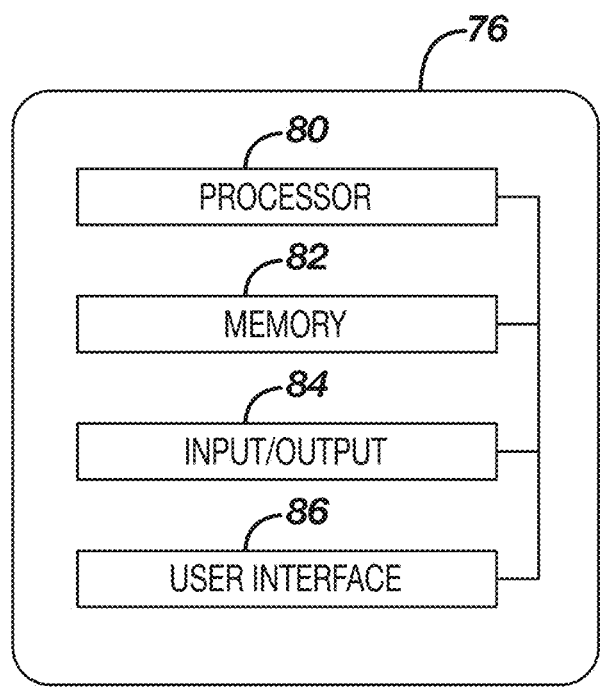
FIG. 10 shows a computing system 76 according to one example that can be used to implement various steps of the methods of FIGS. 2, 7, and 9.

Turning to FIG. 10, a computing system 76 is shown according to one example that can be used to implement steps of the methods of FIGS. 2, 7, and 9. The computing system 76 can be a tablet, a desktop computer, a laptop, a server, or any other suitable computing system. The computing system 76 can include at least one processor 80, a memory 82, and an input/output device 84. In some examples, the computing system 76 can include a user interface (UI) 86. The at least one processor 80, memory 82, input/output device 84, and user interface 86 can be coupled together to allow communications therebetween. As should be appreciated, any of the above components may be distributed across one or more separate devices and/or locations.

In various embodiments, the input/output device 84 includes a receiver for receiving data, such as images from an imaging machine, a transmitter for transmitting data, or a combination thereof. The input/output device 84 can be capable of communicating, such as receiving and/or transmitting information pertaining to a communications network such as, for example, the Internet or an Intranet. The communications can be over, for example, a wired or wireless communications channel. As should be appreciated, transmit and receive functionality may also be provided by one or more devices external to the computing system 76.

The at least one processor 80 can include a single processor or more than one processor. Depending upon the exact configuration and type of processor, the memory 82 can be volatile (such as some types of RAM), non-volatile (such as ROM, flash memory, hard disk drive, etc.), or a combination thereof. The computing system 76 can include additional storage (e.g., removable storage and/or non-removable storage) including, but not limited to, tape, flash memory, smart cards, CD-ROM, digital versatile disks (DVD) or other optical storage, magnetic cassettes, magnetic tape, magnetic disk storage or other magnetic storage devices, universal serial bus (USB) compatible memory, or any other medium which can be used to store information. The memory 82 can have instructions stored thereon that, upon execution by the at least one processor 80, cause the computing system 76 to perform various steps of the methods of FIGS. 2, 7, and 9.

The user interface 86 can include inputs that provide the ability to control the computing system 76, via, for example, buttons, soft keys, a mouse, voice actuated controls, a touch screen, movement of the computing system 76, visual cues (e.g., moving a hand in front of a camera on the computing system 76), audio cues, or the like. The user interface 86 may also include, for example, a scanner for scanning of information such as bar codes, QR codes, and RFID tags. The user interface 86 can provide outputs, including visual information (e.g., via a display, a touch screen, or at least one light), audio information (e.g., via speaker), mechanically (e.g., via a vibrating mechanism), or a combination thereof.

Figure 11:
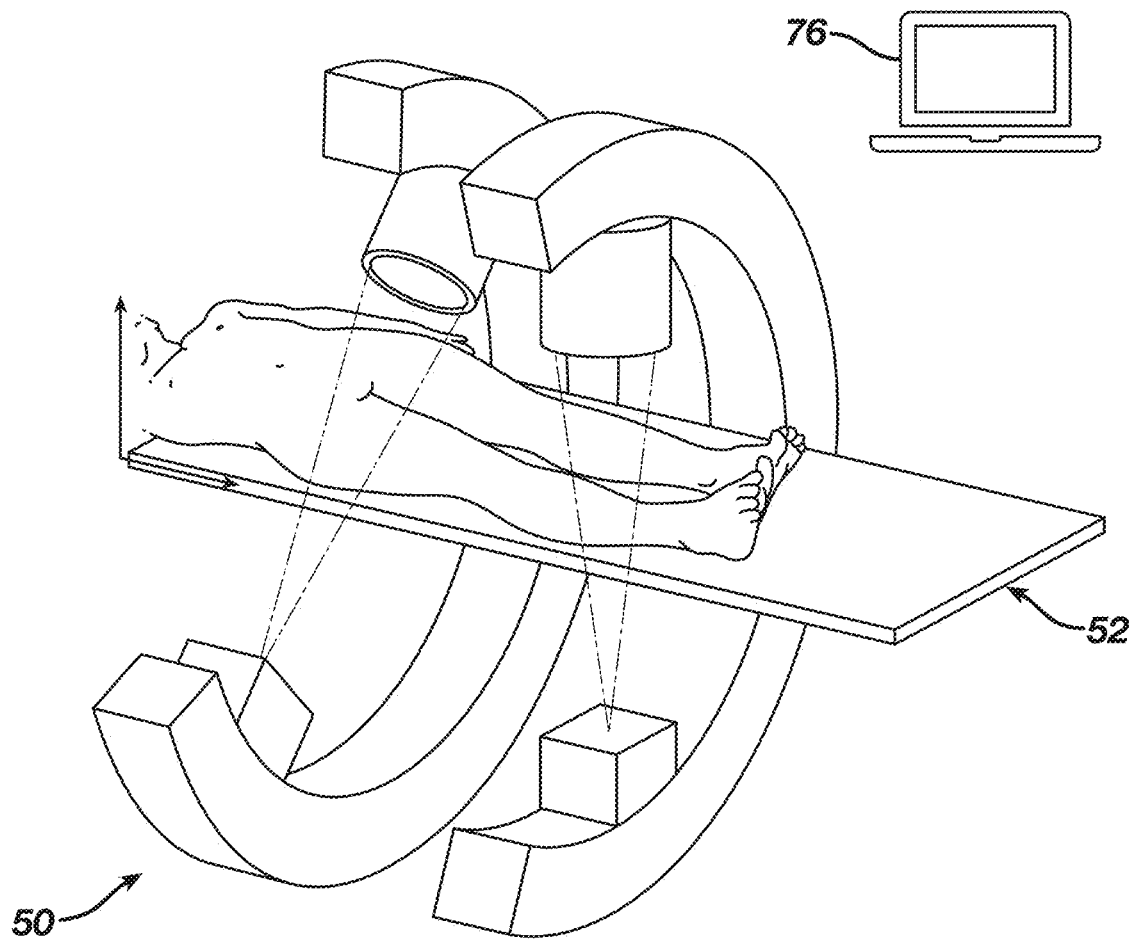
FIG. 11 shows a fracture reduction system according to one example that can be used to implement steps of the methods of FIGS. 2, 7, and 9.

Referring now to FIG. 11, a fracture reduction system is shown according to one example that can be used to implement steps of the methods of FIGS. 2, 7, and 9. The fracture reduction system can comprise the computing system 76 and an imaging device 50. The imaging device 50 can be a C-arm x-ray machine, or any be any other suitable imaging device that generates, for example, x-rays, CT scans, or ultrasound images. In FIG. 11, a C-arm x-ray machine is shown in which two x-ray tubes that are positioned at a fixed angle relative to one another. However, in alternative examples, the C-arm x-ray machine can have a single tube or tubes that are not fixed relative to one another. In other words, examples of the disclosure are not limited to a particular configuration of a C-arm x-ray machine.

The fracture reduction system can include on operating bed or table 52 on which the patient lies during the fracture reduction. Unlike some conventional fracture reduction procedures, the operating bed or table 52 need not have coordinates marked thereon to perform the fracture reduction.

EXAMPLES

Various embodiments of the present disclosure will be understood with reference to the following examples.

Example I: A method, comprising:
  imaging, intraoperatively, a fractured bone of a patient to obtain a first representation of the fractured bone in a computing system, the fractured bone defining at least a first bone fragment, and a second bone fragment that is separated from the first bone fragment by a fracture;
  imaging, intraoperatively, a contralateral bone of the patient to obtain a second representation of the contralateral bone in the computing system;
  generating, intraoperatively in the computing system, a mirrored representation of the first representation or the second representation; and
  comparing, intraoperatively in the computing system, 1) the first representation to a representation of a desired orientation of the fractured bone, wherein the representation of the desired orientation is the mirrored representation of the second representation, or 2) the mirrored representation to the representation of the desired orientation of the fractured bone, wherein the representation of the desired orientation is the second representation, to develop a comparison for use in reducing the fracture.

Example IA. The method of Example I, wherein the step of imaging the fractured bone comprises imaging the fractured bone one or more times to obtain one or more images of the fractured bone.

Example IA1. The method of Example IA, wherein the one or more images comprises x-ray images, CT images, or ultrasound images.

Example IA2. The method of any of Examples IA to IA1, wherein the one or more images comprise a plurality of images, the plurality of images comprising at least 1) a first image taken at a first angle relative to the fractured bone and 2) a second image taken at a second angle relative to the fractured bone, different from the first angle.

Example IA3. The method of Example IA2, wherein the first and second images are taken at angles that are substantially perpendicular to one another.

Example IA4. The method of any of Examples IA3 and IA3, wherein one of the first and second images is taken along an anterior-posterior direction and the other one of the first and second images is taken along a lateral-medial direction.

Example IA5. The method of any of Examples IA to IA4, wherein the one or more images comprises a plurality of images, each corresponding to a different portion of the fractured bone, and the step of obtaining the first representation comprises generating the first representation by combining the plurality of images.

Example IA6. The method of any of Examples I to IA5, wherein the step of obtaining the first representation comprises generating, in the computing system, a first computer model of the fractured bone from one or more images of the fractured bone.

Example IA7. The method of any of Examples I to IA6, wherein the step of obtaining the first representation comprises generating, in the computing system, a set of digital data that characterizes a shape of the fractured bone from one or more images of the fractured bone.

Example IB. The method of any of Examples I to IA7, wherein the step of imaging the contralateral bone comprises a step of imaging the contralateral bone one or more times to obtain one or more images of the contralateral bone.

Example IB1. The method of Example IB, wherein the one or more images comprises x-ray images, CT images, or ultrasound images.

Example IB2. The method of any of Examples IB to IB1, wherein the one or more images comprise a plurality of images, the plurality of images comprising at least 1) a first image taken at a first angle relative to the contralateral bone and 2) a second image taken at a second angle relative to the contralateral bone, different from the first angle.

Example IB3. The method of Example IB2, wherein the first and second images are taken at angles that are substantially perpendicular to one another.

Example IB4. The method of any of Examples IB2 and IB3, wherein one of the first and second images is taken along an anterior-posterior direction and the other one of the first and second images is taken along a lateral-medial direction.

Example IB5. The method of any of Examples IB to IB4, wherein the one or more images comprises a plurality of images, each corresponding to a different portion of the contralateral bone, and the step of obtaining the second representation comprises generating the second representation by combining the plurality of images.

Example IB6. The method of any of Examples I to IB5, wherein the step of imaging the contralateral bone comprises generating, in the computer system, a second computer model of the contralateral bone from one or more images of the contralateral bone.

Example IB7. The method of any of Examples I to IB6, wherein the step of imaging the contralateral bone comprises generating, in the computer system, a set of digital data that characterizes a shape of the contralateral bone.

Example IC. The method of any of Examples I to IB7, wherein the comparing step comprises registering the first representation and the representation of the desired orientation of the fractured bone to one another.

Example IC1. The method of Example IC, wherein the first representation is a computer model and the representation of the desired orientation is an image.

Example IC2. The method of Example IC, wherein the first representation and the representation of the desired orientation are each computer models.

Example IC3. The method of Example IC, wherein the first representation and the representation of the desired orientation are each data sets.

Example IC4. The method of any of Examples IC to IC3, wherein the registering step comprises aligning the first representation and the representation of the desired orientation with one another by matching fiduciary markers of the first representation with fiduciary markers of the representation of the desired orientation.

Example IC5. The method of Example IC4, wherein the fiduciary markers of the first representation and the representation of the desired orientation are defined by anatomical features of the fractured bone and the contralateral bone.

Example IC6. The method of Example IC4, wherein the fiduciary markers of the first representation and the representation of the desired orientation are defined by artificial markers that are attached to the fractured bone and contralateral bone.

Example IC7. The method of any of Examples I to IB7, wherein the comparing step comprises registering the first mirrored representation and the desired orientation of the fractured bone to one another.

Example IC8. The method of Example IC7, wherein the first mirrored representation is a computer model and the representation of the desired orientation is an image.

Example IC9. The method of Example IC7, wherein the first mirrored representation and the representation of the desired orientation are each computer models.

Example IC10. The method of Example IC7, wherein the first mirrored representation and the representation of the desired orientation are each data sets.

Example IC11. The method of any of Examples IC7 to IC10, wherein the registering step comprises aligning the first mirrored representation and the representation of the desired orientation with one another by matching fiduciary markers of the first mirrored representation with fiduciary markers of the representation of the desired orientation.

Example IC12. The method of Example IC11, wherein the fiduciary markers of the first mirrored representation and the representation of the desired orientation are defined by anatomical features of the fractured bone and contralateral bone.

Example IC13. The method of Example IC11, wherein the fiduciary markers of the first mirrored representation and the representation of the desired orientation are defined by artificial markers that are attached to the fractured bone and contralateral bone.

Example ID1. The method of any of Examples I to IC13, comprising generating, in the computer system, a set of one or more malalignment parameters.

Example ID2. The method of Example ID1, comprising a step of adjusting the fracture based on the set of one or more malalignment parameters.

Example ID3. The method of any of Examples ID1 and ID2, wherein the set of one or more malalignment parameters comprises a parameter that corresponds to a difference in length between the fractured bone and the contralateral bone.

Example ID4. The method of any of Examples ID1 to ID3, wherein the set of one or more malalignment parameters comprises a parameter that corresponds to a width of the fracture measured from one bone fragment of the fractured bone to another bone fragment of the fractured bone.

Example ID5. The method of any of Examples ID1 to ID4, wherein the set of one or more malalignment parameters comprises a parameter that corresponds to a difference in rotation between one of the first and second bone fragments and a corresponding portion of the contralateral bone about an axis that extends along a lateral-medial direction.

Example ID6. The method of any of Examples ID1 to ID5, wherein the set of one or more malalignment parameters comprises a parameter that corresponds to a difference in rotation between one of the first and second bone fragments and a corresponding portion of the contralateral bone about an axis that extends along an anterior-posterior direction.

Example ID7. The method of any of Examples ID1 to ID6, wherein the set of one or more malalignment parameters comprises a parameter that corresponds to a difference in rotation between one of the first and second bone fragments and a corresponding portion of the contralateral bone about an axis that extends along a cranial-caudal direction.

Example IE. An electronic fracture reduction system, the system comprising:
  a computing system comprising:
    a processor; and
    memory in communication with the processor, the memory having instructions stored thereon that, upon execution by the processor, cause the computing system to perform operations comprising the method of any of Examples I to ID7.

Example II. A method, comprising:
  obtaining a first representation of the fractured bone in a computing system, the fractured bone defining at least a first bone fragment, and a second bone fragment that is separated from the first bone fragment by a fracture of an articular surface of the fractured bone;
  obtaining a second representation of a contralateral bone of the patient in the computing system;
  generating a mirrored representation of one of the first and second representations in the computing system by mirroring the one of the first and second representations; and
  comparing, in the computing system, the mirrored representation to the other one of the first and second representations to develop a comparison for use in reducing the fracture to conform the articular surface to a desired shape.

Example IIA. The method of Example II, wherein the step of obtaining the first representation comprises obtaining one or more images of the fractured bone.

Example IIA1. The method of Example IIA, wherein the step of obtaining the first representation comprises a step of imaging the fractured bone one or more times.

Example IIA2. The method of any of Examples IIA and IIA1, wherein the step of obtaining the first representation comprises receiving the one or more images of the fractured bone in the computing system.

Example IIA3. The method of any of Examples IIA to IIA2, wherein the one or more images comprises x-ray images, CT images, or ultrasound images.

Example IIA4. The method of any of Examples IIA to IIA3, wherein the one or more images comprise a plurality of images, the plurality of images comprising at least 1) a first image taken at a first angle relative to the fractured bone and 2) a second image taken at a second angle relative to the fractured bone, different from the first angle.

Example IIA5. The method of Example IIA4, wherein the first and second images are taken at angles that are substantially perpendicular to one another.

Example IIA6. The method of any of Examples IIA4 and IIA5, wherein one of the first and second images is taken along an anterior-posterior direction and the other one of the first and second images is taken along a lateral-medial direction.

Example IIA7. The method of any of Examples IIA to IIA6, wherein the one or more images comprises a plurality of images, each corresponding to a different portion of the fractured bone, and the step of obtaining the first representation comprises generating the first representation by combining the plurality of images.

Example IIA8. The method of any of Examples II to IIA7, wherein the step of obtaining the first representation comprises obtaining a first computer model of the fractured bone generated from one or more images of the fractured bone.

Example IIA9. The method of Example IIA8, wherein the step of obtaining the first representation comprises generating, in the computing system, the first computer model from the one or more images.

Example IIA10. The method of any of Examples II to IIA9, wherein the step of obtaining the first representation comprises obtaining a set of digital data that characterizes a shape of the fractured bone.

Example IIB. The method of any of Examples II to IIA10, wherein the step of obtaining the second representation comprises obtaining one or more images of the contralateral bone.

Example IIBB1. The method of Example IIB, wherein the step of obtaining the second representation comprises a step of imaging the contralateral bone one or more times.

Example IIB2. The method of any of Examples IIB and IIB1, wherein the step of obtaining the second representation comprises receiving the one or more images of the contralateral bone in the computing system.

Example IIB3. The method of any of Examples IIB to IIB2, wherein the one or more images comprises x-ray images, CT images, or ultrasound images.

Example IIB4. The method of any of Examples IIB to IIB3, wherein the one or more images comprise a plurality of images, the plurality of images comprising at least 1) a first image taken at a first angle relative to the contralateral bone and 2) a second image taken at a second angle relative to the contralateral bone, different from the first angle.

Example IIB5. The method of Example IIB4, wherein the first and second images are taken at angles that are substantially perpendicular to one another.

Example IIB6. The method of any of Examples IIB4 and IIB5, wherein one of the first and second images is taken along an anterior-posterior direction and the other one of the first and second images is taken along a lateral-medial direction.

Example IIB7. The method of any of Examples IIB to IIB6, wherein the one or more images comprises a plurality of images, each corresponding to a different portion of the contralateral bone, and the step of obtaining the second representation comprises generating the second representation by combining the plurality of images.

Example IIB8. The method of any of Examples II to IIB7, wherein the step of obtaining the second representation comprises obtaining a second computer model of the contralateral bone generated from one or more images of the contralateral bone.

Example IIB9. The method of Example IIB8, wherein the step of obtaining the second representation comprises generating, in the computing system, the second computer model from the one or more images.

Example IIB10. The method of any of Examples II to IIB9, wherein the step of obtaining the second representation comprises obtaining a set of digital data that characterizes a shape of the contralateral bone.

Example IIC. The method of any of Examples II to IIB10, wherein the comparing step comprises registering the first representation and the representation of the desired orientation of the fractured bone to one another.

Example IIC1. The method of Example IIC, wherein the first representation is a computer model and the representation of the desired orientation is an image.

Example IIC2. The method of Example IIC, wherein the first representation and the representation of the desired orientation are each computer models.

Example IIC3. The method of Example IIC, wherein the first representation and the representation of the desired orientation are each data sets.

Example IIC4. The method of any of Examples IIC to IIC3, wherein the registering step comprises aligning the first representation and the representation of the desired orientation with one another by matching fiduciary markers of the first representation with fiduciary markers of the representation of the desired orientation.

Example IIC5. The method of Example IIC4, wherein the fiduciary markers of the first representation and the representation of the desired orientation are defined by anatomical features of the fractured bone and contralateral bone.

Example IIC6. The method of Example IIC4, wherein the fiduciary markers of the first representation and the representation of the desired orientation are defined by artificial markers that are attached to the fractured bone and contralateral bone.

Example IIC7. The method of any of Examples II to IIB10, wherein the comparing step comprises registering the first mirrored representation and the desired orientation to one another.

Example IIC8. The method of Example IIC7, wherein the first mirrored representation is a computer model and the representation of the desired orientation is an image.

Example IIC9. The method of Example IIC7, wherein the first mirrored representation and the representation of the desired orientation are each computer models.

Example IIC10. The method of Example IIC7, wherein the first mirrored representation and the representation of the desired orientation are each data sets.

Example IIC11. The method of any of Examples IIC7 to IIC10, wherein the registering step comprises aligning the first mirrored representation and the representation of the desired orientation with one another by matching fiduciary markers of the first mirrored representation with fiduciary markers of the representation of the desired orientation.

Example IIC12. The method of Example IIC11, wherein the fiduciary markers of the first mirrored representation and the representation of the desired orientation are defined by anatomical features of the fractured bone and contralateral bone.

Example IIC13. The method of Example IIC11, wherein the fiduciary markers of the first mirrored representation and the representation of the desired orientation are defined by artificial markers that are attached to the fractured bone and contralateral bone.

Example IID. The method of any of Examples II to IIC13, wherein the comparing step comprises generating, in the computer system, a set of one or more malalignment parameters.

Example IID1. The method of Example IID, comprising a step of adjusting the fracture based on the set of one or more malalignment parameters.

Example IID2. The method of any of Examples IID to IID1, wherein the set of one or more malalignment parameters comprises a parameter that corresponds to a difference in length between the fractured bone and the contralateral bone.

Example IID3. The method of any of Examples IID to IID2, wherein the set of one or more malalignment parameters comprises a parameter that corresponds to a width of the fracture measured from one bone fragment of the fractured bone to another bone fragment of the fractured bone.

Example IID4. The method of any of Examples IID to IID3, wherein the set of one or more malalignment parameters comprises a parameter that corresponds to a difference in rotation between a portion of the fractured bone and a corresponding portion of the contralateral bone about an axis that extends along a lateral-medial direction.

Example IID5. The method of any of Examples IID to IID4, wherein the set of one or more malalignment parameters comprises a parameter that corresponds to a difference in rotation between a portion of the fractured bone and a corresponding portion of the contralateral bone about an axis that extends along an anterior-posterior direction.

Example IID6. The method of any of Examples IID to IDD5, wherein the set of one or more malalignment parameters comprises a parameter that corresponds to a difference in rotation between a portion of the fractured bone and a corresponding portion of the contralateral bone about an axis that extends along a cranial-caudal direction.

Example IIE. An electronic fracture reduction system, the system comprising:
a computing system comprising:
a processor; and
memory in communication with the processor, the memory having instructions stored thereon that, upon execution by the processor, cause the computing system to perform operations comprising the method of any of Examples II to IID6.

Example III. A method, comprising:
obtaining, in a computing system, a first computer representation of a patient's limb having a fractured bone and an adjacent bone, the first representation including 1) a representation of at least a portion of the fractured bone that includes a fracture and 2) a representation of at least a portion of the adjacent bone;
obtaining, in the computing system, a second computer representation of a contralateral limb of the patient, the second computer representation including a representation of at least a portion of a first contralateral bone, corresponding to the fractured bone, and at least a portion of a second contralateral bone, corresponding to the adjacent bone;
generating, in the computing system, a mirrored representation of the first representation or the second representation; and
comparing, in the computing system, 1) the first representation to a representation of a desired orientation of the limb, wherein the representation of the desired orientation is the mirrored representation of the second representation, or 2) the mirrored representation of the first representation to the representation of the desired orientation of the limb, wherein the representation of the desired orientation is the second representation, to develop a comparison for use in reducing the fracture.

Example IIIA. The method of Example III, wherein the step of obtaining the first representation comprises obtaining one or more images of the limb.

Example IIIA1. The method of Example IIIA, wherein the step of obtaining the first representation comprises a step of imaging the limb one or more times.

Example IIIA2. The method of any of Examples IIIA and IIIA1, wherein the step of obtaining the first representation comprises receiving the one or more images of the limb in the computing system.

Example IIIA3. The method of any of Examples IIIA to IIIA2, wherein the one or more images comprises x-ray images, CT images, or ultrasound images.

Example IIIA4. The method of any of Examples IIIA to IIIA3, wherein the one or more images comprise a plurality of images, the plurality of images comprising at least 1) a first image taken at a first angle relative to the limb and 2) a second image taken at a second angle relative to the limb, different from the first angle.

Example IIIA5. The method of Example IIIA4, wherein the first and second images are taken at angles that are substantially perpendicular to one another.

Example IIIA6. The method of any of Examples IIIA4 and IIIA5, wherein one of the first and second images is taken along an anterior-posterior direction and the other one of the first and second images is taken along a lateral-medial direction.

Example IIIA7. The method of any of Examples IIIA to IIIA6, wherein the one or more images comprises a plurality of images, each corresponding to a different portion of the limb, and the step of obtaining the first representation comprises generating the first representation by combining the plurality of images.

Example IIIA8. The method of any of Examples III to IIIA7, wherein the step of obtaining the first representation comprises obtaining a first computer model of the limb generated from one or more images of the limb.

Example IIIA9. The method of Example IIIA8, wherein the step of obtaining the first representation comprises generating, in the computing system, the first computer model from the one or more images.

Example IIIA10. The method of any of Examples III to IIIA9, wherein the step of obtaining the first representation comprises obtaining a set of digital data that characterizes a shape of the limb.

Example IIIB. The method of any of Examples III to IIIA10, wherein the step of obtaining the second representation comprises obtaining one or more images of the contralateral limb.

Example IIIB1. The method of Example IIIB, wherein the step of obtaining the second representation comprises a step of imaging the contralateral limb one or more times.

Example IIIB2. The method of any of Examples IIIB and IIIB1, wherein the step of obtaining the second representation comprises receiving the one or more images of the contralateral limb in the computing system.

Example IIIB3. The method of any of Examples IIIB to IIIB2, wherein the one or more images comprises x-ray images, CT images, or ultrasound images.

Example IIIB4. The method of any of Examples IIIB to IIIB3, wherein the one or more images comprise a plurality of images, the plurality of images comprising at least 1) a first image taken at a first angle relative to the contralateral limb and 2) a second image taken at a second angle relative to the contralateral limb, different from the first angle.

Example IIIB5. The method of Example IIIB4, wherein the first and second images are taken at angles that are substantially perpendicular to one another.

Example IIIB6. The method of any of Examples IIIB4 and BIBS, wherein one of the first and second images is taken along an anterior-posterior direction and the other one of the first and second images is taken along a lateral-medial direction.

Example IIIB7. The method of any of Examples IIIB to IIIB6, wherein the one or more images comprises a plurality of images, each corresponding to a different portion of the contralateral limb, and the step of obtaining the second representation comprises generating the second representation by combining the plurality of images.

Example IIIB8. The method of any of Examples III to IIIB7, wherein the step of obtaining the second representation comprises obtaining a second computer model of the contralateral limb generated from one or more images of the contralateral limb.

Example IIIB9. The method of Example IIIB8, wherein the step of obtaining the second representation comprises generating, in the computing system, the second computer model from the one or more images.

Example IIIB10. The method of any of Examples III to IIIB9, wherein the step of obtaining the second representation comprises obtaining a set of digital data that characterizes a shape of the contralateral limb.

Example IIIC. The method of any of Examples III to IIIB10, wherein the comparing step comprises registering the first representation and the representation of the desired orientation of the limb to one another.

Example IIIC1. The method of Example IIIC, wherein the first representation is a computer model and the representation of the desired orientation is an image.

Example IIIC2. The method of Example IIIC, wherein the first representation and the representation of the desired orientation are each computer models.

Example IIIC3. The method of Example IIIC, wherein the first representation and the representation of the desired orientation are each data sets.

Example IIIC4. The method of any of Examples IIIC to IIIC3, wherein the registering step comprises aligning the first representation and the representation of the desired orientation with one another by matching fiduciary markers of the first representation with fiduciary markers of the representation of the desired orientation.

Example IIIC5. The method of Example IIIC4, wherein the fiduciary markers of the first representation and the representation of the desired orientation are defined by anatomical features of the limb and contralateral limb.

Example IIIC6. The method of Example IIIC4, wherein the fiduciary markers of the first representation and the representation of the desired orientation are defined by artificial markers that are attached to the limb and contralateral limb.

Example IIIC7. The method of any of Examples III to IIIB10, wherein the comparing step comprises registering the first mirrored representation and the desired orientation of the limb to one another.

Example IIIC8. The method of Example IIIC7, wherein the first mirrored representation is a computer model and the representation of the desired orientation is an image.

Example IIIC9. The method of Example IIIC7, wherein the first mirrored representation and the representation of the desired orientation are each computer models.

Example IIIC10. The method of Example IIIC7, wherein the first mirrored representation and the representation of the desired orientation are each data sets.

Example IIIC11. The method of any of Examples IIIC7 to IIIC10, wherein the registering step comprises aligning the first mirrored representation and the representation of the desired orientation with one another by matching fiduciary markers of the first mirrored representation with fiduciary markers of the representation of the desired orientation.

Example IIIC12. The method of Example IIIC11, wherein the fiduciary markers of the first mirrored representation and the representation of the desired orientation are defined by anatomical features of the limb and contralateral limb.

Example IIIC13. The method of Example IIIC11, wherein the fiduciary markers of the first mirrored representation and the representation of the desired orientation are defined by artificial markers that are attached to the limb and contralateral limb.

Example IIID1. The method of any of Examples III to IIIC13, comprising generating, in the computer system, a set of one or more malalignment parameters.

Example IIID2. The method of Example IIID1, comprising a step of adjusting the fracture based on the set of one or more malalignment parameters.

Example IIID3. The method of any of Examples IIID1 and IIID2, wherein the set of one or more malalignment parameters comprises a parameter that corresponds to a difference in length between the limb and the contralateral limb.

Example IIID4. The method of any of Examples IIID1 to IIID3, wherein the set of one or more malalignment parameters comprises a parameter that corresponds to a width of the fracture measured from one bone fragment of the fractured bone to another bone fragment of the fractured bone.

Example IIID5. The method of any of Examples IIID1 to IIID4, wherein the set of one or more malalignment parameters comprises a parameter that corresponds to a difference in rotation between a portion of the fractured limb and a corresponding portion of the contralateral limb about an axis that extends along a lateral-medial direction.

Example IIID6. The method of any of Examples IIID1 to IIID5, wherein the set of one or more malalignment parameters comprises a parameter that corresponds to a difference in rotation between a portion of the fractured limb and a corresponding portion of the contralateral limb about an axis that extends along an anterior-posterior direction.

Example IIID7. The method of any of Examples IIID1 to IIID6, wherein the set of one or more malalignment parameters comprises a parameter that corresponds to a difference in rotation between a portion of the fractured limb and a corresponding portion of the contralateral limb about an axis that extends along a cranial-caudal direction.

Example IIIE. An electronic fracture reduction system, the system comprising:
a computing system comprising:
a processor; and
memory in communication with the processor, the memory having instructions stored thereon that, upon execution by the processor, cause the computing system to perform operations comprising the method of any of claims III to IID7.

It should be noted that the illustrations and descriptions of the examples and embodiments shown in the figures are for exemplary purposes only, and should not be construed limiting the disclosure. One skilled in the art will appreciate that the present disclosure contemplates various embodiments. Additionally, it should be understood that the concepts described above with the above-described examples and embodiments may be employed alone or in combination with any of the other examples and embodiments described above. It should further be appreciated that the various alternative examples and embodiments described above with respect to one illustrated embodiment can apply to all examples and embodiments as described herein, unless otherwise indicated.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth.

While certain example embodiments have been described, these embodiments have been presented by way of example only and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

It should be appreciated that the subject matter presented herein may be implemented as a computer process, a computer-controlled apparatus, or a computing system or an article of manufacture, such as a computer-readable storage medium. Those skilled in the art will also appreciate that the subject matter described herein may be practiced on or in conjunction with other computer system configurations beyond those described herein, including multiprocessor systems, microprocessor-based or programmable consumer electronics, minicomputers, mainframe computers, handheld computers, personal digital assistants, e-readers, cellular telephone devices, special purposed hardware devices, network appliances, and the like. The embodiments described herein may also be practiced in distributed computing environments, where tasks are performed by remote processing devices that are linked through a communications network. In a distributed computing environment, program modules may be located in both local and remote memory storage devices.

Each of the processes, methods, and algorithms described in the preceding sections may be embodied in, and fully or partially automated by, code modules executed by one or more computers or computer processors. The code modules may be stored on any type of non-transitory computer-readable medium or computer storage device, such as hard drives, solid state memory, optical disc, and/or the like. The processes and algorithms may be implemented partially or wholly in application-specific circuitry. The results of the disclosed processes and process steps may be stored, persistently or otherwise, in any type of non-transitory computer storage such as, e.g., volatile or non-volatile storage.

What is claimed:

1. A method, comprising:
imaging, intraoperatively, a fractured bone of a patient to obtain a first representation of the fractured bone in a computing system, the fractured bone defining at least a first bone fragment, and a second bone fragment that is separated from the first bone fragment by a fracture of an articular surface of the fractured bone;
imaging, intraoperatively, a contralateral bone of the patient to obtain a second representation of the contralateral bone in the computing system;
generating, intraoperatively in the computing system, a mirrored representation of the first representation or the second representation; and
comparing, intraoperatively in the computing system, 1) the first representation to a representation of a desired orientation of the fractured bone, wherein the representation of the desired orientation is the mirrored representation of the second representation, or 2) the mirrored representation to the representation of the desired orientation of the fractured bone, wherein the representation of the desired orientation is the second representation, to develop a comparison for use in reducing the fracture.

2. The method of claim 1, wherein the step of imaging the fractured bone comprises imaging the fractured bone to obtain a plurality of images comprising at least 1) a first image taken at a first angle relative to the fractured bone and 2) a second image taken at a second angle relative to the fractured, different from the first angle.

3. The method of claim 1, wherein obtaining the first representation comprises generating a first computer model of the fractured bone from one or more images of the fractured bone.

4. The method of claim 1, wherein the step of imaging the contralateral bone comprises a step or imaging the contralateral bone to obtain a plurality or images comprising at least 1) a first image taken at a first angle relative to the contralateral bone and 2) a second image taken at a second angle relative to the contralateral bone, different from the first angle.

5. The method of claim 1, wherein the step of imaging the contralateral bone comprises generating, in the computer system, a second computer model of the contralateral bone from one or more images of the contralateral bone.

6. The method of claim 1, wherein the comparing step comprises registering the first representation and the representation of the desired orientation of the fractured bone to one another.

7. The method of claim 6, wherein the registering step comprises aligning the first representation and the representation of the desired orientation with one another by matching fiduciary markers of the first representation with fiduciary markers of the representation of the desired orientation.

8. The method of claim 7, comprising generating, in the computer system, a set of one or more malalignment parameters.

9. The method of claim 8, comprising a step of adjusting the fracture based on the set of one or more malalignment parameters.

10. The method of claim 9, wherein the set of one or more malalignment parameters comprises a parameter that corresponds to a difference in length between the fractured bone and the contralateral bone.

11. The method of claim 9, wherein the set of one or more malalignment parameters comprises a parameter that corresponds to a width of the fracture measured from one bone fragment of the fractured bone to another bone fragment of the fractured bone.

12. The method of claim 9, wherein the set of one or more malalignment parameters comprises a parameter that corresponds to a difference in rotation between one of the first and second bone fragments and a corresponding portion of the contralateral bone about one or more of (1) an axis that extends along a lateral-medial direction, (2) an axis that extends along an anterior-posterior direction, and (3) an axis that extends along a cranial-caudal direction.

13. A method, comprising:
obtaining a first representation of a fractured bone in a computing system, the fractured bone defining at least a first bone fragment, and a second bone fragment that is separated from the first bone fragment by a fracture of an articular surface of the fractured bone;
obtaining a second representation of a contralateral bone of the patient in the computing system;
generating a mirrored representation of one of the first and second representations in the computing system by mirroring the one of the first and second representations; and
comparing, in the computing system, the mirrored representation to the other one of the first and second representations to develop a comparison for use in reducing the fracture to conform the articular surface to a desired shape.

14. The method of claim 13, wherein the step of obtaining the first representation comprises obtaining a plurality of images comprising at least 1) a first image taken at a first angle relative to the fractured bone and 2) a second image taken at a second angle relative to the fractured bone, different from the first angle.

15. The method of claim 13, wherein the step of obtaining the first representation comprises obtaining a first computer model of the fractured bone generated from one or more images of the fractured bone.

16. The method of claim 13, wherein the step of obtaining the second representation comprises obtaining a plurality of images comprising at least 1) a first image taken at a first angle relative to the contralateral bone and 2) a second image taken at a second angle relative to the contralateral bone, different from the first angle.

17. The method of claim 13, wherein the step of obtaining the second representation comprises obtaining a second computer model of the contralateral bone generated from one or more images of the contralateral bone.

18. The method of claim 13, wherein the comparing step comprises registering the first representation and the representation of the desired orientation of the fractured bone to one another.

19. The method of claim 18, wherein the registering step comprises aligning the first representation and the representation of the desired orientation with one another by matching fiduciary markers of the first representation with fiduciary markers of the representation of the desired orientation.

20. The method of claim 13, wherein the comparing step comprises generating, in the computer system, a set of one or more malalignment parameters.

21. The method of claim 20, comprising a step of adjusting the fracture based on the set of one or more malalignment parameters.

22. The method of claim 21, wherein the set of one or more malalignment parameters comprises a parameter that corresponds to a difference in length between the fractured bone and the contralateral bone.

23. The method of claim 21, wherein the set of one or more malalignment parameters comprises a parameter that corresponds to a width of the fracture measured from one bone fragment of the fractured bone to another bone fragment of the fractured bone.

24. The method of claim 21, wherein the set of one or more malalignment parameters comprises a parameter that corresponds to a difference in rotation between a portion of the fractured bone and a corresponding portion of the contralateral bone about one or more of (1) an axis that extends along a lateral-medial direction, (2) an axis that extends along an anterior-posterior direction, and (3) an axis that extends along a cranial-caudal direction.

\* \* \* \* \*